(12) United States Patent
Flick

(10) Patent No.: US 6,200,284 B1
(45) Date of Patent: Mar. 13, 2001

(54) GELASTIC HEEL CARE DEVICE AND METHOD

(75) Inventor: Roland E. Flick, Elma, NY (US)

(73) Assignee: Gaymar Industries, Inc., Orchard Park, NY (US)

( * ) Notice: Subject to any disclaimer, the term of this patent is extended or adjusted under 35 U.S.C. 154(b) by 0 days.

(21) Appl. No.: 09/336,625

(22) Filed: Jun. 18, 1999

(51) Int. Cl.$^7$ .................................................. A61F 5/00
(52) U.S. Cl. ................................ 602/13; 602/14; 602/27
(58) Field of Search ................................. 602/5, 13, 14, 602/23, 27, 61, 62, 65

(56) References Cited

U.S. PATENT DOCUMENTS

| | | | |
|---|---|---|---|
| 4,964,402 | * 10/1990 | Grim et al. | |
| 5,027,801 | 7/1991 | Grim | 128/80 |
| 5,415,624 | 5/1995 | Williams | 602/21 |
| 5,508,334 | 4/1996 | Chen | 524/474 |
| 5,599,283 | 2/1997 | Lindenmeyer et al. | 602/62 |
| 5,635,201 | 6/1997 | Fabo | 424/443 |

OTHER PUBLICATIONS

European Search Report.

* cited by examiner

Primary Examiner—Michael A. Brown
Assistant Examiner—Lalita N. Hamilton
(74) Attorney, Agent, or Firm—Hodgson, Russ, Andrews, Woods & Goodyear LLP

(57) ABSTRACT

The present invention is a protective and pressure normalizing device for a body extremity. The device has a three-dimensional gelastic member, and a cover. The three-dimensional gelastic member has a predetermined shape to conform to the body extremity and a plurality of openings. The opening are at least positioned on the top side of the gelastic member. The cover encases the gelastic member and is removable therefrom. The cover also has an upper side, a underside, and a plurality of edges which correspond to the shape of the gelastic member. The underside contacts the body extremity, while the upper side has a plurality of connectors designed to bring one edge of the cover to a predetermined distance from another edge of the cover. Thereby, the protective and pressure normalizing device supports the body extremity.

42 Claims, 5 Drawing Sheets

GELASTIC HEEL CARE DEVICE AND METHOD

FIELD OF THE INVENTION

The present invention generally relates to devices and methods for stabilizing and supporting the foot, in particular the heel, of a human body.

BACKGROUND OF THE INVENTION

U.S. Pat. No. 5,489,259 to Jacobs et al. relates to a pressure-normalizing single-chambered static pressure device for supporting and protecting a body extremity, in particular a heel. That device has an inflatable member, a plurality of seams, and apertures along those seams. Those plurality of seams, according to Jacobs et al., "enhance the ability of that device to produce a cradling effect whereby [the] interior surface [of that device] can better engage and fully conform to the contour of the lower extremity." Col 7, lines 6–9 (brackets added for clarity and deleted numbers.) Thus, without those seams that device, according to Jacobs et al., would not adequately cradle the extremity.

A problem with the device disclosed by Jacobs et al. are that it can be easily over-inflated or under-inflated. For example, if the device is properly filled when the outer atmosphere temperature and/or barometric pressure is at level A and these atmospheric events decrease to level A-1, which is lower than A, later that day, the device will appear under-inflated. And if the device appears "under-inflated," the device fails to provide adequate support. And if the user notices the device is under-inflated, which it is not, when the atmospheric events revert to level A and the user inflates the device to appear when it was at level A, the resulting device will be over-inflated when the outer atmospheric temperature returns to level A. An over-inflated device provides too much pressure and can be deleterious to the body extremity.

The present invention solves these problems.

SUMMARY OF THE INVENTION

The present invention is a protective and pressure normalizing device for a body extremity. The device has a gelastic material shaped to contour the desired body extremity, a cover for the gelastic material, and a releasable securing apparatus. The gelastic member and cover are designed to cradle the extremity. Thereby, the gelastic member applies a truly uniform interface pressure where it is applied to the extremity.

BRIEF DESCRIPTION OF THE DRAWINGS

For a further understanding of the invention, as well as its characterizing features, reference should now be made to the accompanying drawings wherein.

DETAILED DESCRIPTION OF THE PRESENT INVENTION

It is an object of the present invention to provide a device and method for stabilizing the ankle while relieving pressure, including shear forces, on the heel of the foot.

A further object of the present invention is to provide a device and method for supporting and stabilizing the ankle and heel of the foot in order to prevent shortening of the Achilles tendon, i.e., "foot drop."

Another object of the present invention is to provide a device and method for supporting and stabilizing the ankle while relieving pressure on the heel. The device being adaptable to fit different sized feet and can be worn on either the left or right foot.

It is a further object of the present invention is to minimize pressure, including shear force, contact between the heel and the surface of a hospital bed, thereby decreasing the risk to the patient of the formation of decubitus ulcers on the heel area as a result of such contact.

A further object of the present invention provides a device for surrounding an ankle and which prevents the extremity from rotating with respect to the leg once the device cradles the extremity.

Another object of the present invention to provides a foot care device which is of simple construction and of a design which is simple and inexpensive to manufacture.

It is a further object of the invention to provide a foot care device which holds the foot securely in the desired position and which supports the foot in a manner which prevents the foot from slipping within the device.

It is another object of the invention to prevent over- or under-inflation of inflatable support devices for body extremities.

Figure 1:
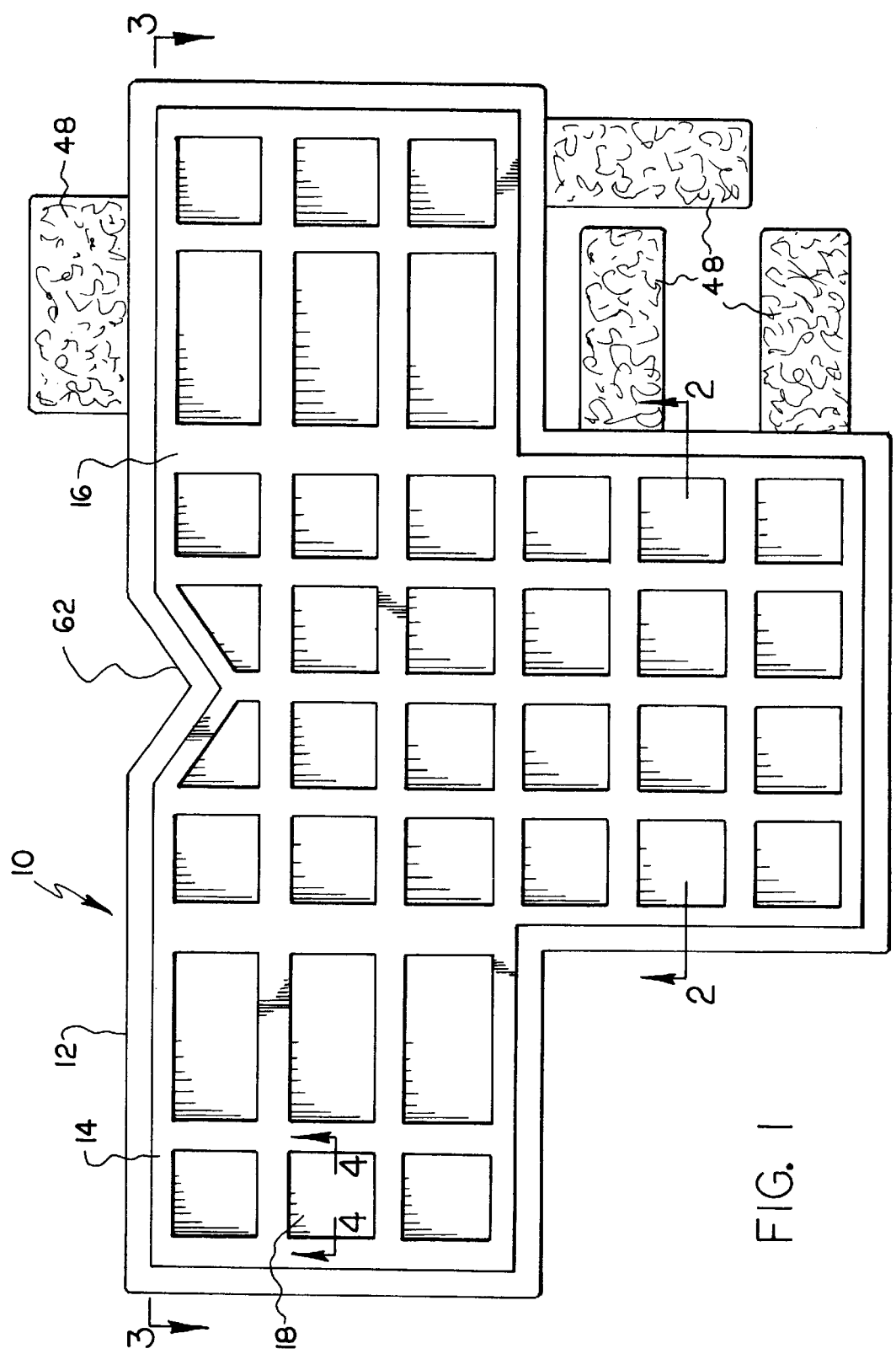
FIG. 1 is a top plan view of the foot care device of the present invention.
Figure 2:
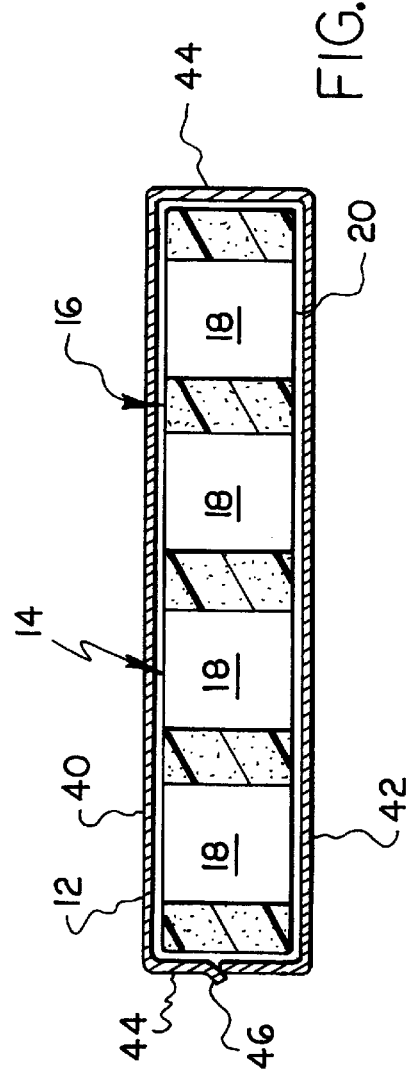
FIG. 2 is a side view of FIG. 1 taken along the line 2—2.
Figure 3:
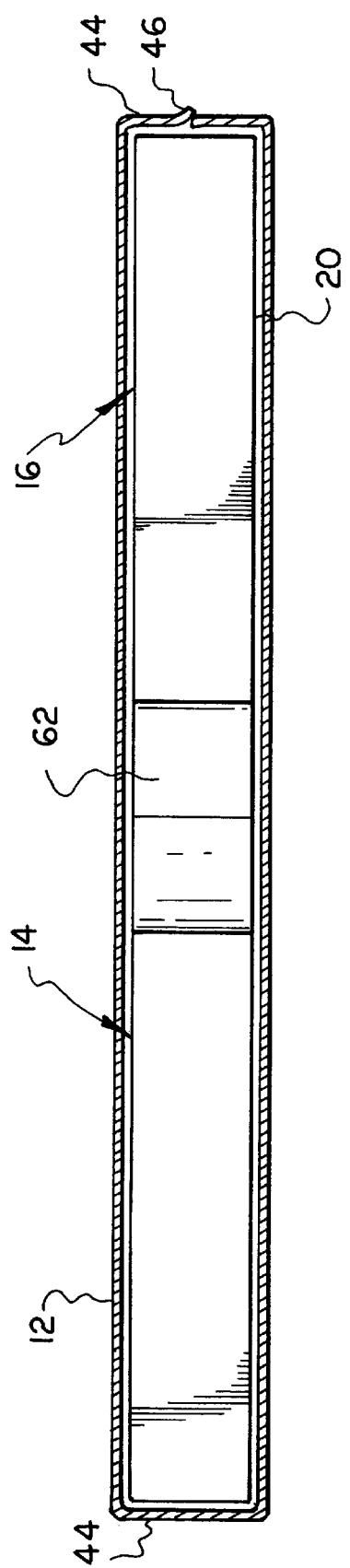
FIG. 3 is a side view of FIG. 1 taken along the line 3—3.

FIG. 1 shows a top plan view of a foot care device 10 according to the present invention. Foot care device 10 has a cover 12 and a three-dimensional gelastic material 14. The cover 12 may be constructed of a lightweight cotton, gauze, paper or synthetic material which may be woven or non-woven material, or any other material which is breathable and suitable for use in a hospital, alternative care, or home care environment, or combinations thereof. The material can also be stretchable, like a sock and worn like a sock. The material must be strong enough to be secured about the foot and leg of a patient, and capable of being comfortably placed in contact with the foot, ankle and/or leg of a patient. The selected material should minimize shear force on the patient's tissue and should provide adequate wicking characteristics such that moisture is drawn away from the skin of the lower leg and foot, keeping the foot and leg at a normal temperature. Further the material must be one of sufficient flexibility and pliability to conform readily to the shape of the patient's foot.

As further described below, the cover 12 has an upper side 40, an underside 42, a releasable seal 46, and a plurality of edges 44a, 44b, 44c, 44d, 44e, 44f which correspond to the shape of the gelastic material 14. The underside 42 contacts the body extremity, while the upper side 40 has a plurality of releasable securing apparatuses 48, as shown in FIGS. 1–3 and 9. The underside 42 and upper side 40 can be the same material or different materials. In either case, one of the seams to join the underside 42 to the upper side 40 is a releasable seal 46. The releasable seal 46 allows the gelastic material 14 to be removably inserted within the cover 12. Acceptable releasable seals include zippers, tongue and groove systems, and hook and loop systems.

The releasable securing apparatuses 48 are designed to bring one edge 44 of the cover 12 to a desired distance from another edge 44 of the cover 12 so the device 10 properly supports the body extremity. For example, combination of edges 44 that correspond with each other, include 44a–44b, 44c–44d, and 44e–44f. The releasable securing apparatuses 48 can be a conventional hook and loop structures, buckle and latch systems, aperatures and string system, or any other conventional releasable securing apparatus.

Figure 8:
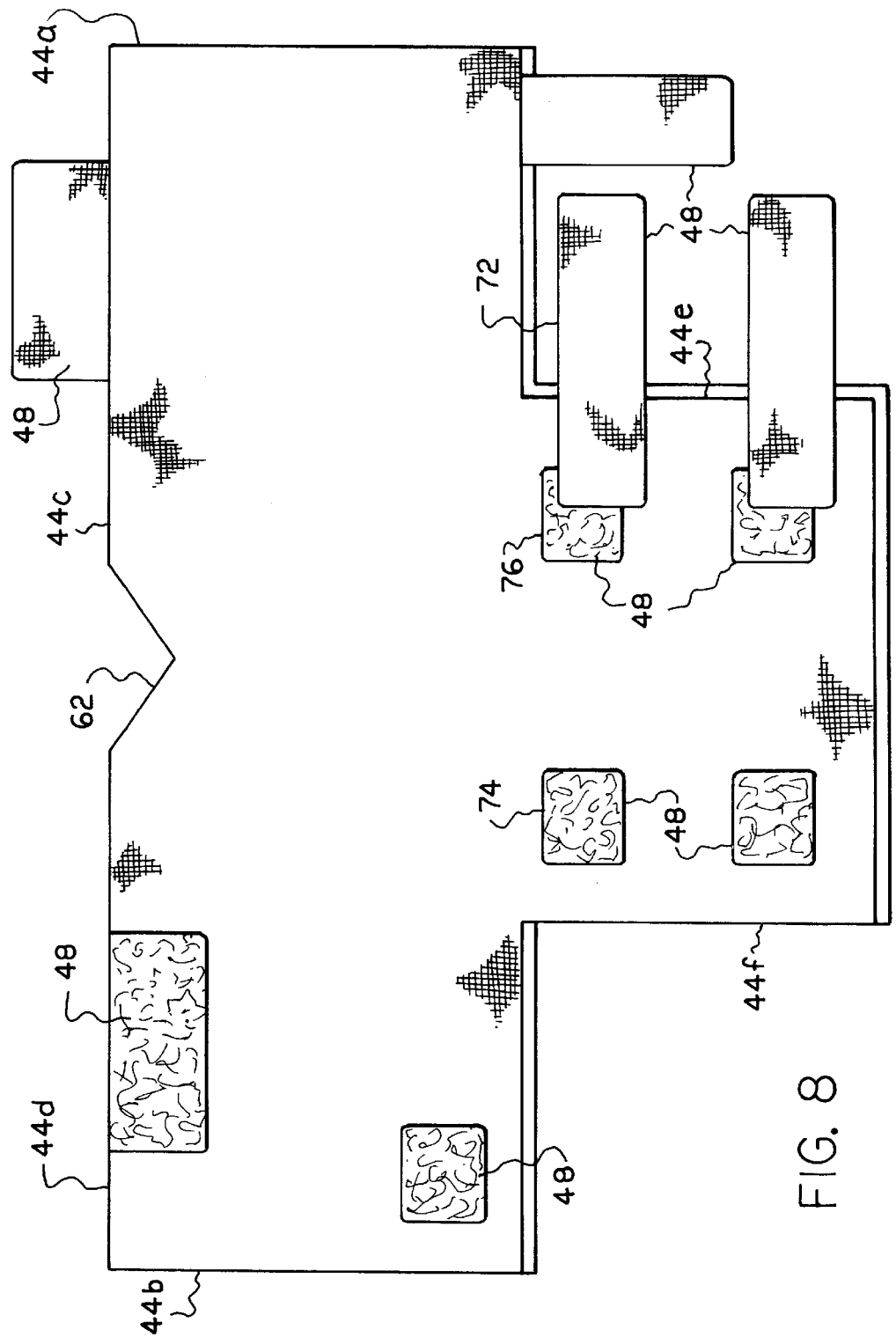
FIG. 8 is top view of the cover.

A detailed example of one type of the releasable securing apparatus 48 is illustrated in FIG. 8. The example relates to a type of hook and loop system which has a strap 72 and two tabs 74, 76. Each tab 74, 76 is positioned near an edge 44 (in particular 44e, 44f) to receive the corresponding strap 72. The strap 72, in return, releasably secures edges 44f and 44e to a desired distance from each other.

Gelastic material 14 used in the present invention is fully disclosed in U.S. Pat. Nos. 4,369,284, 4,618,213, 5,262,468, 5,336,708, and 5,508,334, (the inventor in each patent is Chen) which are hereby incorporated by reference herein. These patents disclose the various embodiments of the gelatinous elastomer material. This gelastic material 14 has many attributes that are sufficiently set forth in the cited patents.

Figure 4:
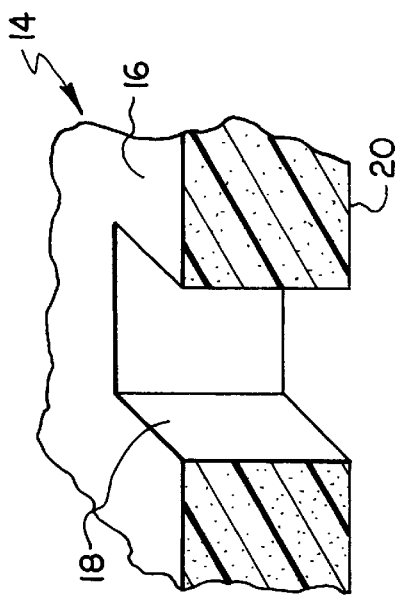
FIG. 4 is a cross-sectional view of FIG. 1 taken along the line 4—4.
Figure 5:
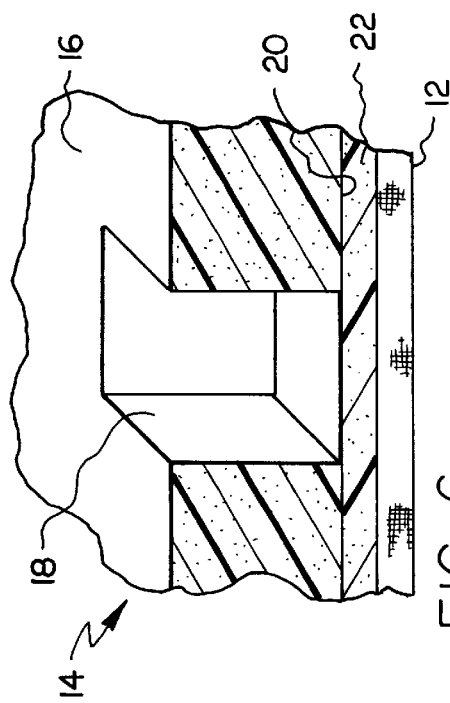
FIG. 5 is an alternative embodiment of FIG. 4.

The material 14 has a bottom side 20 which is only shown in FIGS. 2–7, and a top side 16 which has a plurality of openings 18. The openings 18 either extend through the gelastic material 14 as shown in FIG. 5, or extend through only a portion of the gelastic material 14 as shown in FIG. 4. In either case, the gelastic material 14 should have a backing material 22 in order to maintain the structure and desired shape for the device 10.

Figure 7:
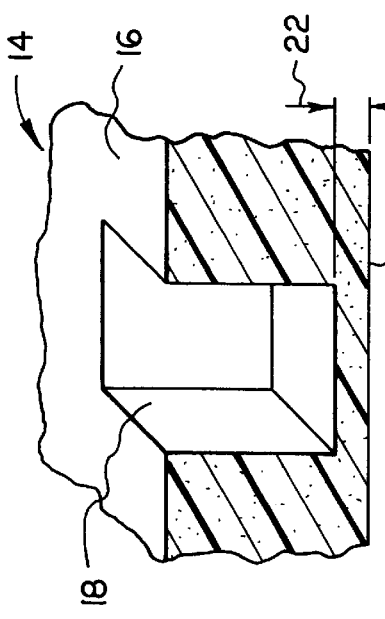
FIG. 7 is another alternative embodiment of FIG. 4.
Figure 6:
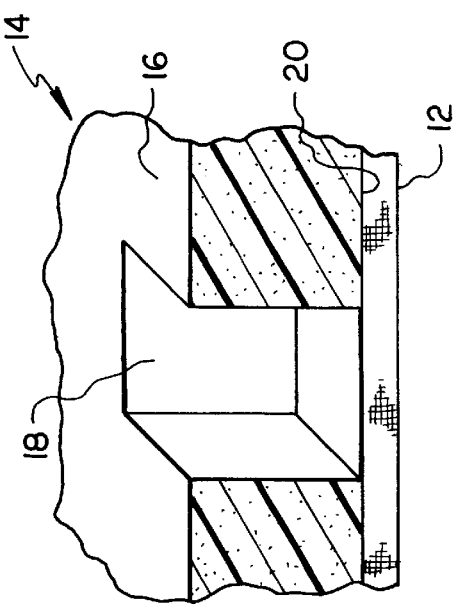
FIG. 6 is an alternative embodiment of FIG. 4.

The backing material 22 can be the gelastic material 14, 22—no distinct layer—as shown in FIG. 4, the cover 12, 22 as shown in FIG. 7, or a third material 22 which is distinct from the gelastic material 14 or cover material 12. The third material 22 can be the same or different material as the cover material 12 or gelastic material 14, the third material 22 just has to be a distinct layer. The backing material 22 maintains the structure and desired shape of the gelastic material 14 when the backing material 22 is attached to the bottom side 20. The backing material 22 can be attached by any conventional manner, such as adhesives, hook & loop, staples, or melting the backing material 22 to the bottom side 20.

Preferably, the gelastic material 14 is seamless. In some instances, the gelastic material 14 requires a seam. When a seam is required, the gelastic material 14 has a first and a second gelatinous materials 14a, 14b, a first permeable layer 30, and a control gap 32. The first and second gelatinous materials 14a, 14b each have at least one connecting side 34a, 34b. The connecting side 34a of the first gelatinous material and the connecting side 34b of the second gelatinous material are adjacent to each other so the first and second materials 14a, 14b are essentially side-by-side within the same horizontal plane. The first permeable layer 30 has a top side 36 and a bottom side 38. The top side 36 attaches to the first and second connecting sides 34a, 34b. The control gap 32 is interspaced between the bottom side 38 of the first permeable layer 30. This gap 32 degrades the rigidity between each connecting side 34a, 34b and provides an equivalent structural property throughout the gelastic material 14.

Figure 9:
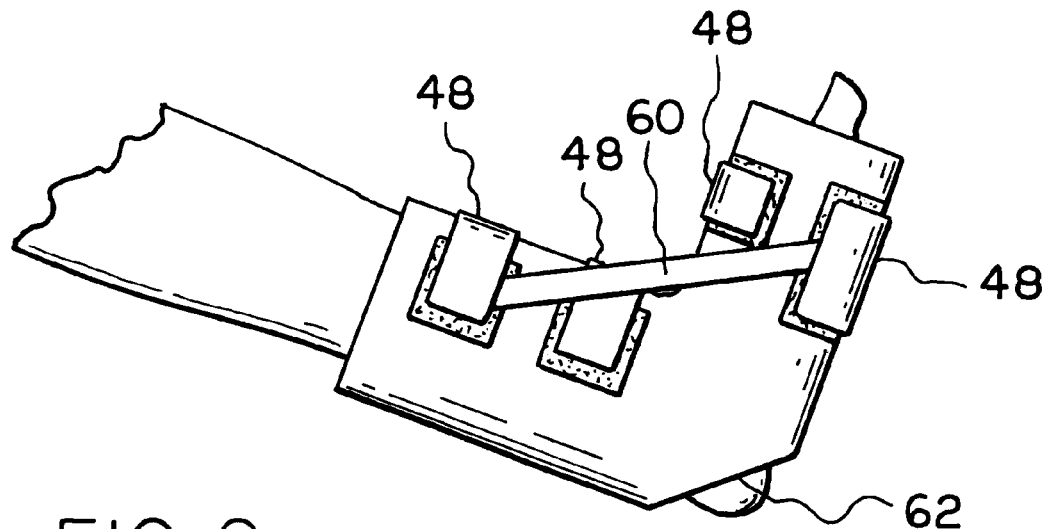
FIG. 9 is a perspective view of the FIG. 1, as it appears secured about the leg, ankle, and foot of a person.
Figure 10:
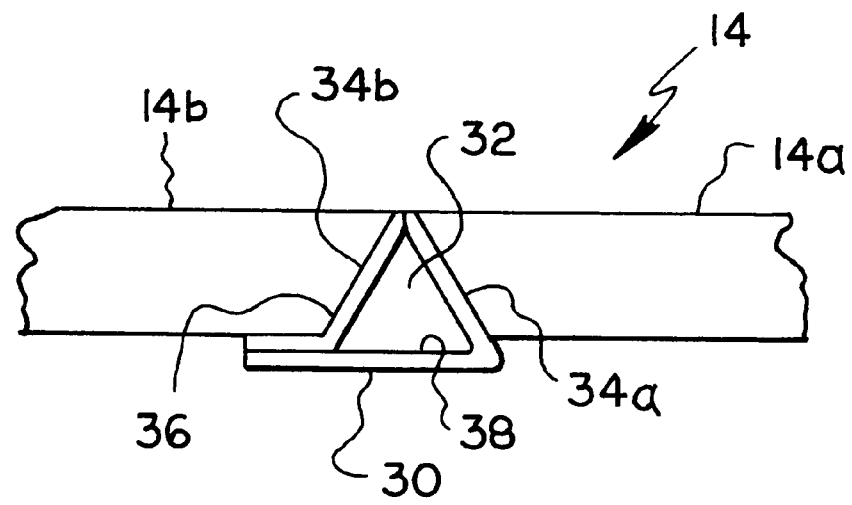
FIG. 10 is an alternative embodiment of the gelastic material 14.

The gelastic material 14 is configured to cradle and provide support to a patient's foot, ankle, arm, elbow, knee, or leg, as illustrated in FIGS. 1 and 9. In other words, the gelastic material 14 forms a soft, flexible supporting cushion around the body extremity in such a manner as to hold the extremity securely and comfortably in a position which minimizes pressure on the extremity, like a heel and/or ankle. In this manner, formations of decubitus ulcers on the heel and/or ankle are substantially prevented.

To provide comfort to the patient, the gelastic material 14 can be inserted into the cover 12 by two distinct manners. If the body extremity is to be warmed, it is preferred the top side 16 of the gelastic material 14 contacts the underside 42 of the cover 12. And if the body extremity is to be cooled, it is preferred the top side 16 of the gelastic material 14 contacts the upper side 40 of the cover 12. The difference in temperature felt by the patient is due to the backing material 22 on the gelastic material 14.

To provide further support, the device can have a support connection 60, which is an alternate version of the releasable securing mechanism 48, as shown in FIG. 9. The support connection 60 ensures the body extremity retains the desired position and can be adjusted between any of the releasable securing mechanisms 48.

To exchange air between the body extremity and the surrounding atmosphere, the device 10 has an aperture 62. In particular, aperture 62 is adapted to receive the heel of a patient, the heel and/or ankle being inserted there through, thereby permitting observation of the condition of the patient's heel without removing device 10.

Alternatively, the gelastic material 14 can be designed to conform to a specific individual's foot, or to a generic foot design. In other words, the gelastic material 14 can be contoured to release the stress and pressure to the ankle bone, Achilles tenden, and other portions of the foot which are in contact with the gelastic material 14. Moreover, the device 10 can have multiple sizes for different foot sizes.

Alternatively, the device 10 can be designed to secure a forearm, elbow, and upper arm, in the same way it is illustrated in FIG. 9 for a foot.

Alternatively, when the cover 12 is a sock-like apparatus the cover need not encase the entire gelastic material 14. Rather the cover 12 need only contact one side of the gelastic material 14, as shown in FIG. 7. Moreover, the cover would not require a releasable securing mechanism 48 in such an embodiment of the present invention.

Although a preferred embodiment of the invention has been disclosed in detail for illustrative purposes, it will be recognized that there are variations of modifications of the preferred embodiment, including the rearrangement of parts, which lie within the scope of the present invention.

What is claimed is:

1. A protective and pressure normalizing device for a body extremity, the device comprising:

a three-dimensional gelastic member having at least a top side, a bottom side, and a plurality of openings which are at least positioned on the top side, the gelastic member has a predetermined shape to conform to the body extremity;

the plurality of openings form resilient exterior and interior walls so when a predetermined pressure of the body extremity is applied to at least one of the walls, the at least one of the walls bends into at least one opening adjacent to the at least one of the walls; and a cover that encases the gelastic member and is removable therefrom, the cover has an upper side, an underside, and a plurality of edges which correspond to the shape of the gelastic member, the underside contacts the body extremity, the upper side has a plurality of releasable securing apparatuses which are designed to bring one edge of the cover to a desired distance from another edge of the cover so the protective and pressure normalizing device supports the body extremity.

2. The device of claim 1 wherein the gelastic member has a backing material covering the bottom side.

3. The device of claim 2 wherein the backing material is the same gelastic material as the gelastic member.

4. The device of claim 2 wherein the backing material is a different gelastic material than the gelastic member.

5. The device of claim 2 wherein the backing material is a distinct layer from than the cover and gelastic member.

6. The device of claim 2 wherein the backing material is the cover.

7. The device of claim 1 wherein the openings extend from the top side through the bottom side.

8. The device of claim 1 wherein the top side of the gelastic member contacts the underside of the cover, and the bottom side of the gelastic member contacts the upper side of the cover.

9. The device of claim 1 wherein the bottom side of the gelastic member contacts the underside of the cover, and the top side of the gelastic member contacts the upper side of the cover.

10. The device of claim 1 further comprising a support connection to ensure the position of the body extremity.

11. The device of claim 1 further comprising an aperture for a part of the body extremity.

12. The device of claim 11 wherein the part of the body extremity is a heel.

13. The device of claim 1 wherein the gelastic material is seamless.

14. The device of claim 1 wherein the gelastic material has a seam and a control gap between the seam.

15. A method of using a protective and pressure normalizing device for a body extremity, the device having a three-dimensional gelastic member with at least a top side, a bottom side, and a plurality of openings which are at least positioned on the top side, the gelastic member has a predetermined shape to conform to the body extremity; the plurality of openings form resilient exterior and interior walls so when a predetermined pressure of the body extremity is applied to at least one of the walls, the at least one of the walls bends into at least one opening adjacent to the at least one of the walls; and a cover that encases the gelastic member and is removable therefrom, the cover has an upper side, an underside, and a plurality of edges which correspond to the shape of the gelastic member, the upper side has a plurality of releasable securing apparatuses, the method comprising the steps of:

positioning the gelastic member within the cover;

adjusting the underside of the protective and pressure normalizing device so it contacts the body extremity;

attaching the plurality of connectors together to bring one edge of the cover to a desired distance from another edge of the cover so the protective and pressure normalizing device supports the body extremity.

16. The method of claim 15 wherein the gelastic member has a backing material covering the bottom side.

17. The method of claim 16 wherein the backing material is the same gelastic material as the gelastic member.

18. The method of claim 16 wherein the backing material is a different gelastic material than the gelastic member.

19. The method of claim 16 wherein the backing material is a distinct layer from than the cover and gelastic member.

20. The method of claim 16 wherein the backing material is the cover.

21. The method of claim 15 wherein the openings extend from the top side through the bottom side.

22. The method of claim 15 wherein the top side of the gelastic member contacts the underside of the cover, and the bottom side of the gelastic member contacts the upper side of the cover.

23. The method of claim 15 wherein the bottom side of the gelastic member contacts the underside of the cover, and the top side of the gelastic member contacts the upper side of the cover.

24. The method of claim 15 further comprising a support connection to ensure the position of the body extremity.

25. The method of claim 15 further comprising an aperture for a part of the body extremity.

26. The method of claim 25 wherein the part of the body extremity is a heel.

27. The method of claim 15 wherein the gelastic material is seamless.

28. The method of claim 15 wherein the gelastic material has a seam and a control gap between the seam.

29. A protective and pressure normalizing device for a body extremity, the device comprising:

a three-dimensional gelastic member having at least a top side, a bottom side, and a plurality of openings which are at least positioned on the top side, the gelastic member has a predetermined shape to conform to the body extremity;

the plurality of openings form resilient exterior and interior walls so when a predetermined pressure of the body extremity is applied to at least one of the walls, the at least one of the walls bends into at least one opening adjacent to the at least one of the walls; and a cover that encases at least a portion of the gelastic member and is removable therefrom, the cover has an upper side, an underside, and a plurality of edges which correspond to the shape of the gelastic member, the underside contacts the body extremity, the upper side has a plurality of releasable securing apparatuses which are designed to bring one edge of the cover to a desired distance from another edge of the cover so the protective and pressure normalizing device supports the body extremity.

30. The device of claim 29 wherein the gelastic member has a backing material covering the bottom side.

31. The device of claim 30 wherein the backing material is the same gelastic material as the gelastic member.

32. The device of claim 30 wherein the backing material is a different gelastic material than the gelastic member.

33. The device of claim 30 wherein the backing material is a distinct layer from than the cover and gelastic member.

34. The device of claim 30 wherein the backing material is the cover.

35. The device of claim 29 wherein the openings extend from the top side through the bottom side.

36. The device of claim 29 wherein the top side of the gelastic member contacts the underside of a cover, and the bottom side of the gelastic member contacts the upper side of the cover.

37. The device of claim 29 wherein the bottom side of the gelastic member contacts the underside of a cover, and the top side of the gelastic member contacts the upper side of the cover.

38. The device of claim 29 further comprising a support connection to ensure the position of the body extremity.

39. The device of claim 29 further comprising an aperture for a part of the body extremity.

40. The device of claim 39 wherein the part of the body extremity is a heel.

41. The device of claim 29 wherein the gelastic material is seamless.

42. The device of claim 29 wherein the gelastic material has a seam and a control gap between the seam.

* * * * *